US009752981B2

(12) United States Patent
Lee et al.

(10) Patent No.: US 9,752,981 B2
(45) Date of Patent: Sep. 5, 2017

(54) APPARATUS WITH A SPECTRAL REFLECTOMETER FOR PROCESSING SUBSTRATES

(71) Applicant: Lam Research Corporation, Fremont, CA (US)

(72) Inventors: Seonkyung Lee, Mountain View, CA (US); Dmitry Opaits, Fremont, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 15/089,214

(22) Filed: Apr. 1, 2016

(65) Prior Publication Data

US 2016/0320293 A1 Nov. 3, 2016

Related U.S. Application Data

(60) Provisional application No. 62/155,261, filed on Apr. 30, 2015.

(51) Int. Cl.
| | |
|---|---|
| *G01N 21/55* | (2014.01) |
| *G01N 21/27* | (2006.01) |
| *H01J 37/00* | (2006.01) |
| *G01N 21/84* | (2006.01) |

(52) U.S. Cl.
CPC ............ *G01N 21/55* (2013.01); *G01N 21/272* (2013.01); *H01J 37/00* (2013.01); *G01N 2021/8411* (2013.01); *G01N 2201/0633* (2013.01); *G01N 2201/08* (2013.01); *G01N 2201/1222* (2013.01)

(58) Field of Classification Search
CPC ........... G01N 2033/0068; G01N 25/54; G01N 27/127; G01N 27/129; G01N 27/4146; G01N 33/0054; G01N 33/0062; G02B 26/001
See application file for complete search history.

(56) References Cited

U.S. PATENT DOCUMENTS

| | | | | |
|---|---|---|---|---|
| 5,962,852 A | * | 10/1999 | Knuettel | A61B 5/0066 250/339.11 |
| 6,764,379 B2 | | 7/2004 | Finarov | |
| 7,019,844 B2 | | 3/2006 | Venugopal et al. | |
| 7,169,015 B2 | | 1/2007 | Finarov | |
| 7,327,476 B2 | | 2/2008 | Cohen et al. | |
| 7,927,184 B2 | | 4/2011 | Finarov | |
| 2005/0020073 A1 | * | 1/2005 | Perry | G01N 21/272 438/689 |
| 2008/0014748 A1 | | 1/2008 | Perry | |
| 2011/0235056 A1 | * | 9/2011 | Matsudo | G01B 11/06 356/630 |
| 2015/0330631 A1 | * | 11/2015 | Amikura | F23N 5/24 137/6 |

\* cited by examiner

*Primary Examiner* — Michael P Stafira
(74) *Attorney, Agent, or Firm* — Beyer Law Group LLP (57) ABSTRACT

A spectral reflectometer system for measuring a substrate is provided. A light source is provided. At least one optical detector is provided. An optical cable comprises a plurality of optical fibers, wherein the plurality of optical fibers comprises a first plurality of optical fibers, which are transmission optical fibers which extend from the light source to an optical path, and a second plurality of optical fibers, which are reflection optical fibers which extend from the optical path to the at least one optical detector. A microlens array is in the optical path.

17 Claims, 6 Drawing Sheets

APPARATUS WITH A SPECTRAL REFLECTOMETER FOR PROCESSING SUBSTRATES

CROSS REFERENCE TO RELATED APPLICATIONS

This application claims priority to U.S. Provisional Patent Application No. 62/155,261 filed on Apr. 30, 2015 and entitled "APPARATUS WITH A SPECTRAL REFLECTOMETER FOR PROCESSING SUBSTRATES" which is incorporated by reference herein.

BACKGROUND OF THE INVENTION

The present invention relates an apparatus for the formation of semiconductor devices. More specifically, the invention relates to a spectral reflectometer for forming semiconductor devices.

SUMMARY

To achieve the foregoing and in accordance with the purpose of the present disclosure, a spectral reflectometer system for measuring a substrate is provided. A light source is provided. At least one optical detector is provided. An optical cable comprises a plurality of optical fibers, wherein the plurality of optical fibers comprises a first plurality of optical fibers, which are transmission optical fibers which extend from the light source to an optical path, and a second plurality of optical fibers, which are reflection optical fibers which extend from the optical path to the at least one optical detector. A microlens array is in the optical path.

In another manifestation, an apparatus for processing a substrate is provided. A processing chamber is provided. A substrate support for supporting the substrate is within the processing chamber. A spectral reflectometer system comprises a light source, at least one optical detector, an optical cable, comprising a plurality of optical fibers, wherein the plurality of optical fibers comprises a first plurality of optical fibers, which are transmission optical fibers which extend from the light source to an optical path, and a second plurality of optical fibers, which are reflection optical fibers which extend from the optical path to the at least one optical detector, a microlens array in the optical path, wherein the microlens array comprises a plurality of microlens, and an optical assembly supported across the optical path, wherein the optical path is positioned to provide light from the light source to an illuminated portion of the substrate and collect reflected light from the illuminated portion of the substrate, wherein light from the light source and reflected light pass through the microlens array, wherein each microlens of the plurality of microlens has a focal plane, and wherein the illuminated portion of the substrate does not lie on any focal plane of the plurality of microlens.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In the formation of semiconductor devices, a substrate is processed in a processing chamber. A spectral reflectometer may be used to illuminate a portion of a substrates surface to determine if an end point has been reached. An example of such a spectral reflectometer is described in US Patent Application No. 2008/0014748 A1 by Andrew Perry, published on Sep. 19, 2007, which is incorporated by reference for all purposes.

Figure 1:
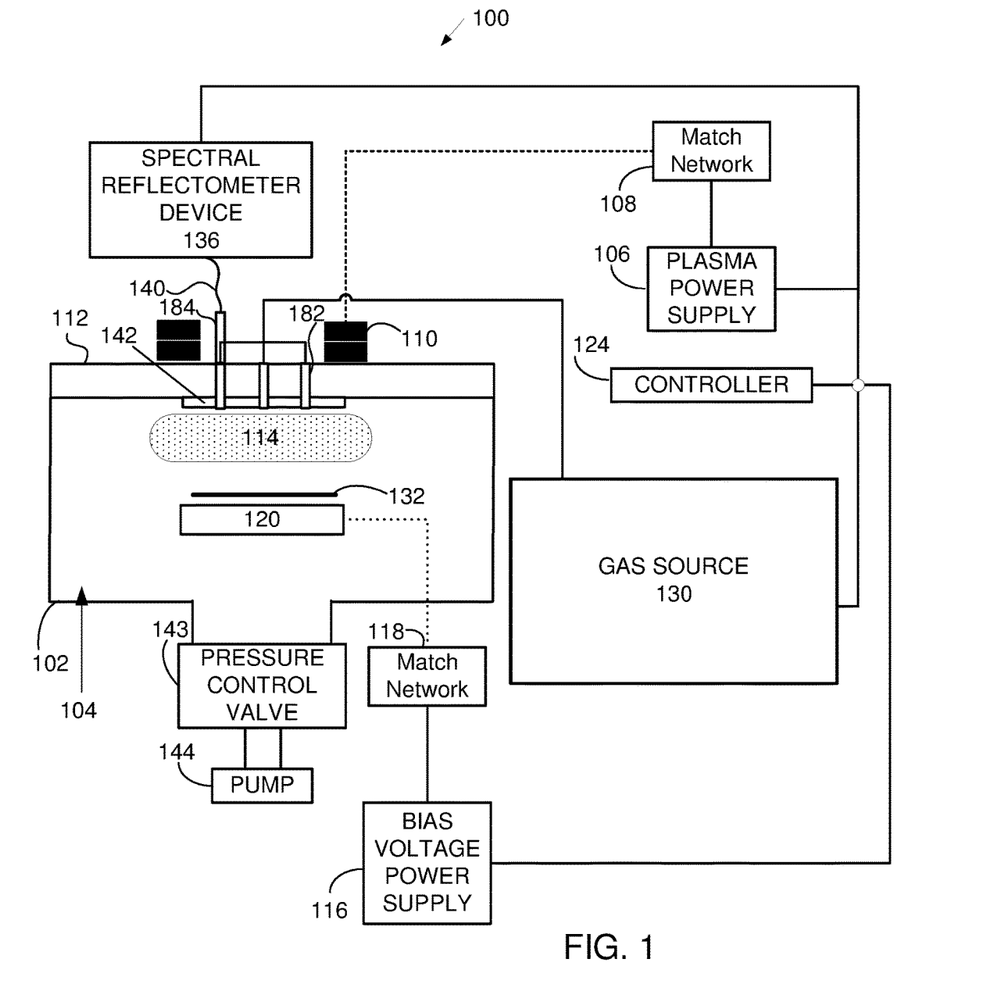
FIG. 1 schematically illustrates an example of a plasma processing system, which uses an embodiment.

FIG. 1 schematically illustrates an example of a plasma processing system 100, which uses an embodiment. The plasma processing system 100 includes a plasma reactor 102 having a plasma processing confinement chamber 104 therein. A plasma power supply 106, tuned by a match network 108, supplies power to a TCP coil 110 located near a power window 112 to create a plasma 114 in the plasma processing confinement chamber 104 by providing an inductively coupled power. The TCP coil (upper power source) 110 may be configured to produce a uniform diffusion profile within the plasma processing confinement chamber 104. For example, the TCP coil 110 may be configured to generate a toroidal power distribution in the plasma 114. The power window 112 is provided to separate the TCP coil 110 from the plasma processing confinement chamber 104 while allowing energy to pass from the TCP coil 110 to the plasma processing confinement chamber 104. A wafer bias voltage power supply 116 tuned by a match network 118 provides power to an electrode in the form of a substrate support 120 to set the bias voltage on the substrate 132 which is supported by the substrate support 120. A controller 124 sets points for the plasma power supply 106, gas source/gas source 130, and the wafer bias voltage power supply 116.

The plasma power supply 106 and the wafer bias voltage power supply 116 may be configured to operate at specific radio frequencies such as, for example, 13.56 MHz, 27 MHz, 2 MHz, 60 MHz, 100 kHz, 2.54 GHz, or combinations thereof. Plasma power supply 106 and wafer bias voltage power supply 116 may be appropriately sized to supply a range of powers in order to achieve desired process performance. In addition, the TCP coil 110 and/or the substrate support 120 may be comprised of two or more sub-coils or sub-electrodes, which may be powered by a single power supply or powered by multiple power supplies.

The gas source 130 is in fluid connection with plasma processing confinement chamber 104 through gas inlets 182 in a shower head 142. The gas inlets 182 may be located in any advantageous location in the plasma processing confinement chamber 104, and may take any form for injecting gas. Preferably, however, the gas inlet may be configured to produce a "tunable" gas injection profile, which allows independent adjustment of the respective flow of the gases to multiple zones in the plasma process confinement chamber 104. The process gases and byproducts are removed from the plasma process confinement chamber 104 via a pressure control valve 143 and a pump 144, which also serve to maintain a particular pressure within the plasma processing confinement chamber 104. The gas source/gas supply mechanism 130 is controlled by the controller 124. A collimator housing 184 is connected to at least one gas inlet 182. An optical cable 140 is connected between the collimator housing and a spectral reflectometer device 136. In this embodiment, the optical cable 140 comprises transmission optical fibers and receiving optical fibers and the spectral reflectometer device 136 houses a xenon arc lamp and photodetectors. Such a xenon arc lamp may provide a pulsed non-uniform beam. The xenon arc lamp is coupled to the transmission optical fibers to provide light to the collimator housing 184. The photodetectors are coupled to the receiving optical fibers to receive reflected, which receives light reflected from the substrate 132. An embodiment of the invention may be used with a Kiyo and Flex by Lam Research Corp. of Fremont, Calif. and with other substrate processing systems.

Figure 2:
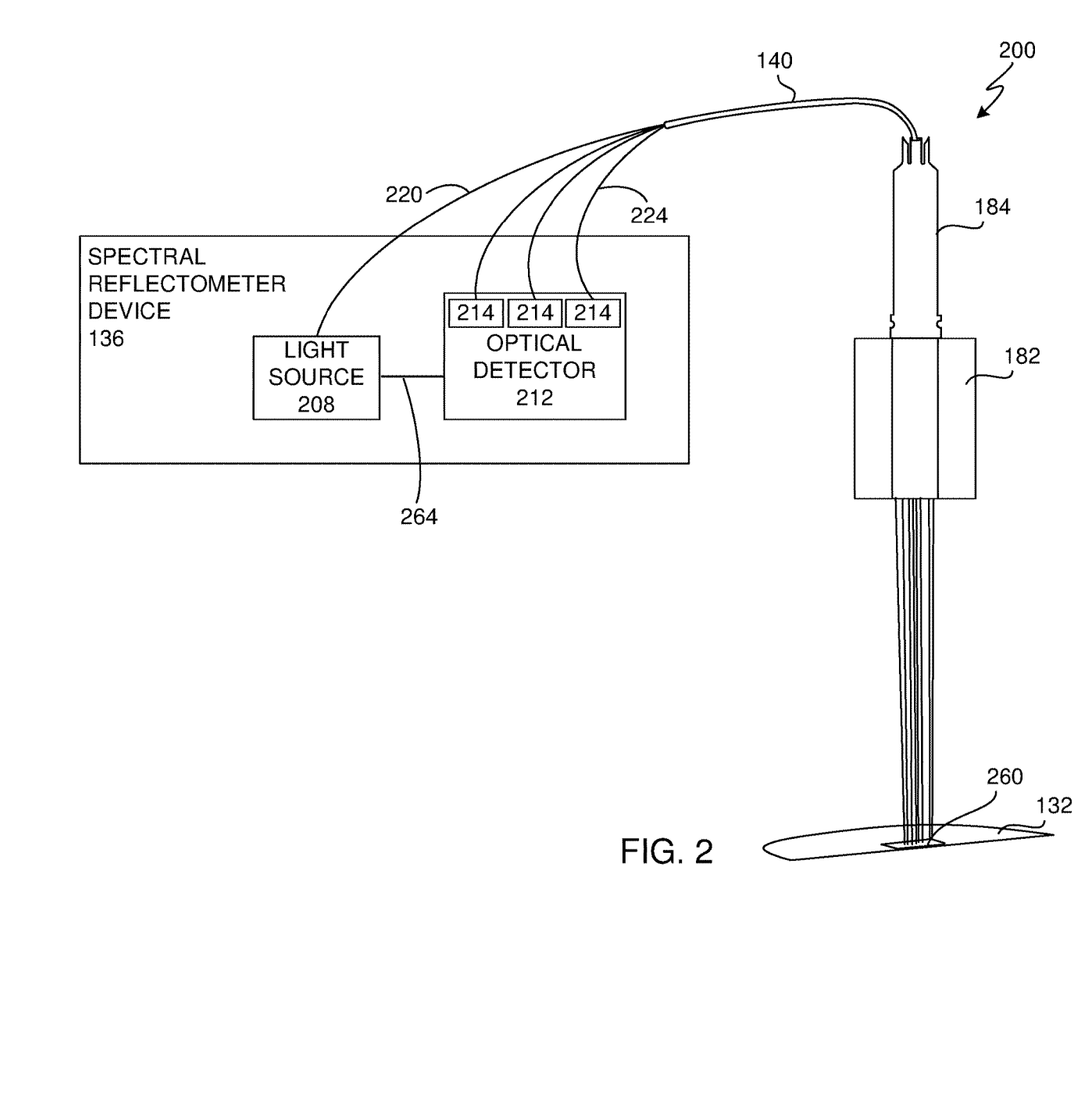
FIG. 2 is a schematic view of a spectral reflectometer system of the plasma processing system.

FIG. 2 is a schematic view of the spectral reflectometer system 200. The spectral reflectometer device 136 comprises a light source 208 and an optical detector 212. The optical detector 212 may comprise one or more photodetectors 214. The fiber optic cable 140 is connected to the spectral reflectometer device. In this example, the optical cable 140 comprises transmission optical fibers 220 and receiving optical fibers 224. In this example each receiving optical fiber 224 is connected to an individual photodetector 214. In other embodiments a plurality of receiving optical fibers 224 may be connected to the same photodetector 214. In this example, the optical detector 212 is a two dimensional charge couple device (2-D CCD) array where an output from each receiving fiber 224 is detected by different regions of the 2-D CCD. For a spectral reflectometer system, the optical detector 212 provides output of intensity as a function of wavelength. This may be accomplished by using a prism or a filter that is able to separate out one or more wavelengths from the reflected light. Light may be directed from the light source 208 to the optical detector 212 through a fiber 264 to allow the monitoring of light source 208 variations over time to correct the signal and improve signal-to-noise ratio (SNR).

Figure 3:
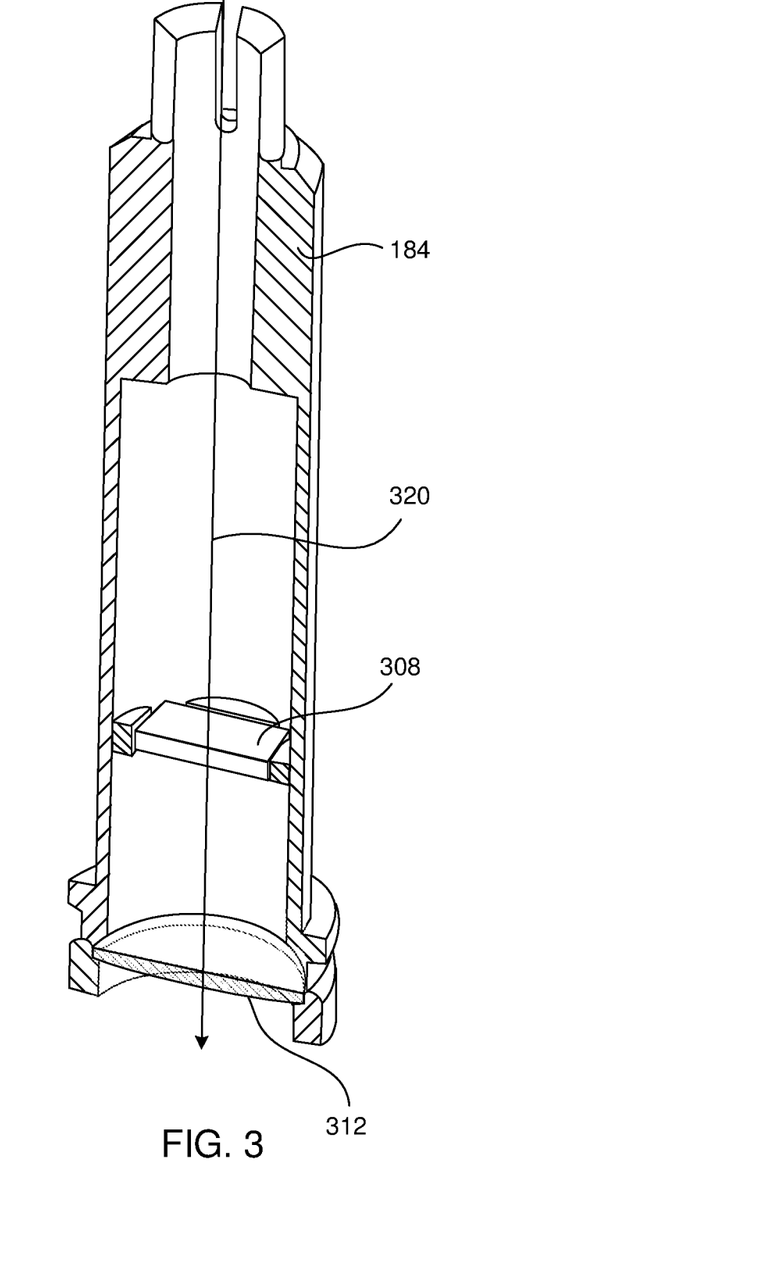
FIG. 3 is a cross-sectional view of a collimator housing of the spectral reflectometer system.
Figure 6:
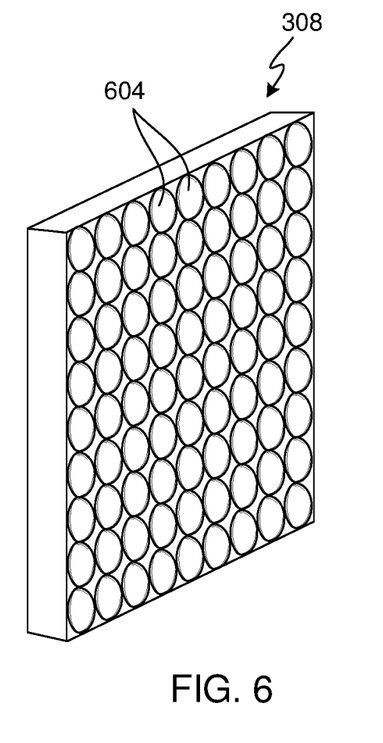
FIG. 6 is an enlarged view of a microlens array of the reflectometer system.

FIG. 3 is a cross-sectional view of the collimator housing 184. Within the collimator housing 184 is a microlens array 308. A microlens array 308 comprises a plurality of adjacent lenses. An example of a microlens array 308 is shown in FIG. 6. In this example, the 10 mm×10 mm microlens array 308 has at least 81 microlens 604. The collimator housing 184 supports a collimator lens 312, which in this embodiment is a single lens that extends across a bore in the collimator housing 184. An optical path 320 extends along the length of the collimator housing 184 from an end of the optical cable 140, through the microlens array 308 and the collimator lens 312, so that the single collimator lens 312 extends completely across the optical path.

Figure 4:
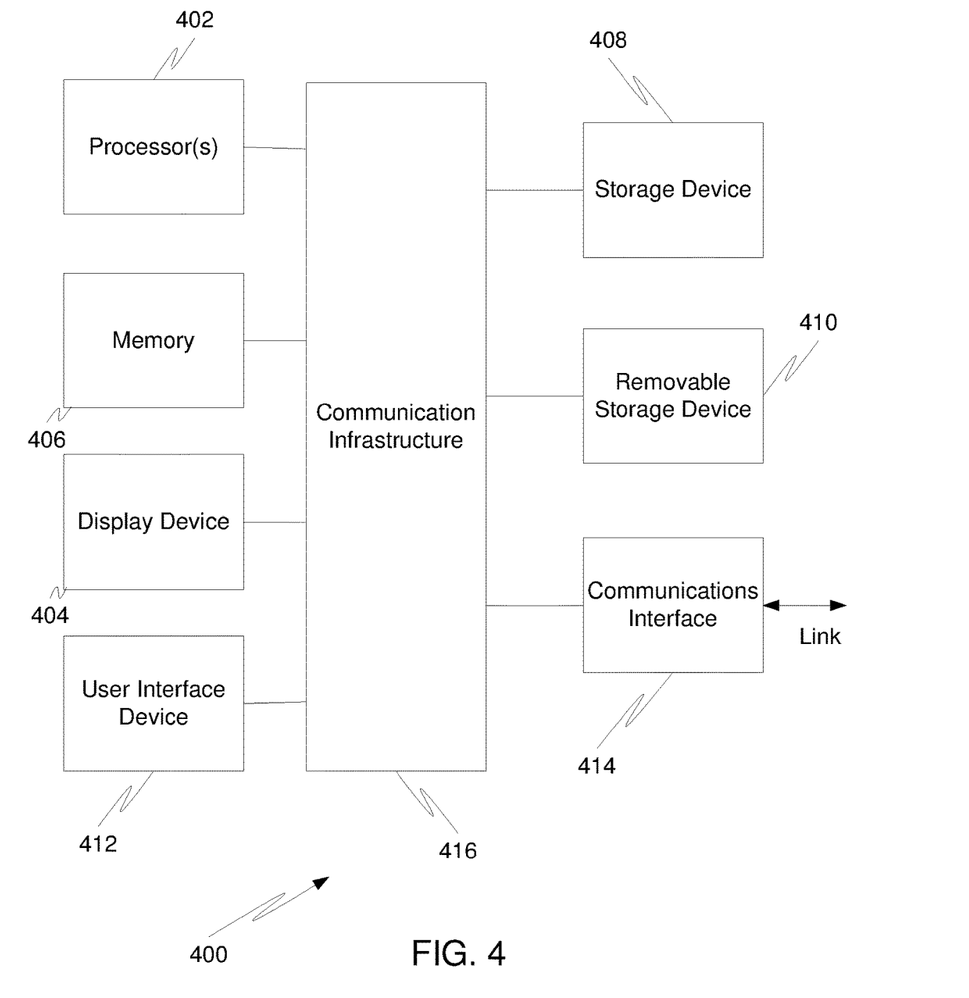
FIG. 4 is a high level block diagram showing a computer system, which is suitable for implementing a controller of the plasma processing system.

FIG. 4 is a high level block diagram showing a computer system 400, which is suitable for implementing the controller 124 used in embodiments of the present invention. The computer system may have many physical forms ranging from an integrated circuit, a printed circuit board, and a small handheld device up to a huge super computer. The computer system 400 includes one or more processors 402, and further can include an electronic display device 404 (for displaying graphics, text, and other data), a main memory 406 (e.g., random access memory (RAM)), storage device 408 (e.g., hard disk drive), removable storage device 410 (e.g., optical disk drive), user interface devices 412 (e.g., keyboards, touch screens, keypads, mice or other pointing devices, etc.), and a communication interface 414 (e.g., wireless network interface). The communication interface 414 allows software and data to be transferred between the computer system 400 and external devices via a link. The system may also include a communications infrastructure 416 (e.g., a communications bus, cross-over bar, or network) to which the aforementioned devices/modules are connected.

Information transferred via communications interface 414 may be in the form of signals such as electronic, electromagnetic, optical, or other signals capable of being received by communications interface 414, via a communication link that carries signals and may be implemented using wire or cable, fiber optics, a phone line, a cellular phone link, a radio frequency link, and/or other communication channels. With such a communications interface, it is contemplated that the one or more processors 402 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 5:
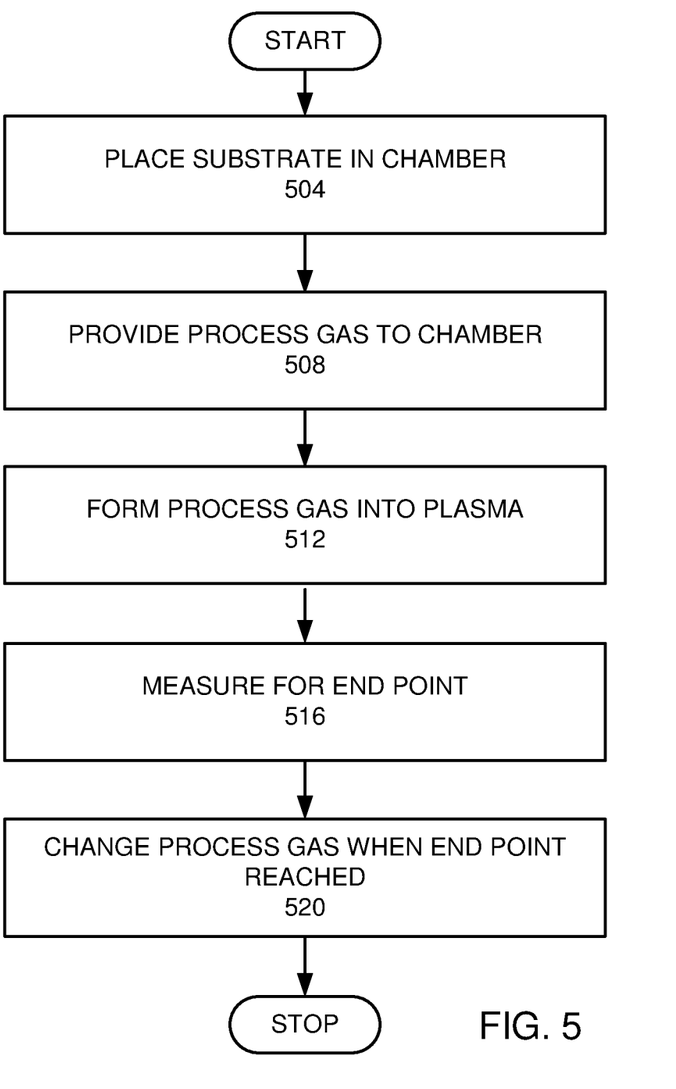
FIG. 5 is a high level flow chart that uses the plasma processing system.

FIG. 5 is a high level flow chart that uses an embodiment. A substrate 132 is placed in the confinement chamber 104 (step 504). In this example, the substrate 132 is mounted on the substrate support 120. A process gas is provided from the gas source 130 into the confinement chamber 104 (step 508). The process gas is formed into a plasma (step 512). The plasma power supply 106 provides power through the match network 108 to the TCP coil 110, which energizes the process gas to form a plasma 114. The plasma 114 may be used to etch the substrate or provide a deposition or perform another process.

The substrate 132 is measured for an endpoint (step 516). Light is generated by the light source 208 and travels from the light source 208 through the transmission optical fibers 220 to the collimator housing 184 along the optical path from the first end of the collimator housing 184, which defines a first end of an optical path, through the microlens array 308 and the collimator lens 312 through the gas inlet 182 to illuminate a portion of a wafer or substrate 132. The mircolenses 604 in the microlens array 308 each have a focal plane. The illuminated portion 260 of the substrate 132 is placed outside of the focal plane, so that the light is not focused but is instead blurred on the illuminated portion 260 of the surface of the wafer 132. A portion of the optical path 320 is perpendicular to the surface of the illuminated portion 260 of the wafer 132, so that some of the light is reflected back to the collimator housing 184, through the collimator lens 312 and the microlens array 308, which then reaches the receiving optical fibers 224 which guide the light to the photodetectors 214. Signals from the photodetectors 214 are sent to the controller 124. The controller 124 uses the signals to determine when an endpoint is reached. In this embodiment the spectra of the reflected light is used to determine when an endpoint is reached.

When the controller 124 detects an endpoint the process gas is changed (step 520). The change in the process gas from the gas source 130 may be accomplished by stopping the flow of the process gas in one embodiment. In another embodiment the change in the process gas may be accomplished by changing concentrations of the component gas, or adding or subtracting at least one component gas. In another embodiment, the process gas may be replaced by another process gas. The substrate 132 may be further processed in the confinement chamber 104 or may be removed from the confinement chamber 104. The plasma processing system 100 uses the spectral reflectometer device 136 to determine endpoint in order to determine when a process change is to be executed.

Tests were performed with the microlens array and without the microlens array. It was found that signal variation was decreased when the microlens array was used. It was found that the mircrolens array provided spectral reproducibility and uniform spatial distribution from alignment to alignment by decreasing the effect of the lamp, fiber, and collimator spatial distortions. The increased uniformity and reproducibility provides for a more uniform process and reduced device defects. UV-compatible optics is used to improve light illumination with spectral spatial distribution from a spatially non-uniform light source.

In other embodiments, the microlens array is placed between the collimator lens and the illuminated portion of the wafer. The collimator lens forms an optical assembly. In other embodiments, the optical assembly may be another single lens that extends across the optical path or alternative optics, such as a concave mirror or a dual or triple lens that extends across the optical path. Additional optical elements, such as a polarizer may be part of the optical assembly in other embodiments. In other embodiments, the processing chamber uses capacitive coupling instead of or in addition to inductive coupling. In other embodiment, the collimator housing is connected to a light access point. In other embodiments the pulsed arc lamp may be replaced by a continuous broadband light source. Some embodiments may use a shutter to control a "pulsing" operation. Other pulsed or continuous broadband light sources may be used. Preferably, the broadband light source is a white light source.

Although a single collimator housing is shown as being offset from the center to illuminating a single portion of the substrate offset from the center is shown in the above embodiment, in other embodiments, the collimator housing may be placed above the center of a substrate. In other embodiments, multiple collimator housings may be provided to illuminate multiple positions on the wafer. In some embodiments, a single spectral reflectometer system may be provided with a single light source and a plurality of optical cables extending from the light source to different collimator housings. In other embodiments, multiple spectral reflectometers may be used where each spectral reflectometer has its own light source. Multiple optical cables may be connected to and share a single detector in some embodiments. In other embodiments each optical cable may have one or more detectors that not shared. In other embodiments, multiple optical cables may share multiple optical detectors.

In the specification and claims, when the optical path is substantially perpendicular to the substrate, the optical path is close enough to perpendicular to the illuminated portion of the substrate so that some of the reflected light from the illuminated portion is reflected back to the microlens array 308. Preferably, most (more than 50% by intensity) of the reflected light from the illuminated portion is reflected back to the microlens array 308. In various embodiments, other housing may be used in place of the collimator housing to hold the optical cable, microlens array, and single lens in the optical path. Such a housing provides support and may be a single component or several components to form the housing. In other embodiments, the spectral reflectometer device may be used for inspecting a substrate that is not within a process chamber. For example, a substrate may be analyzed after being removed from a process chamber.

While this invention has been described in terms of several preferred embodiments, there are alterations, permutations, and various substitute equivalents, which fall within the scope of this invention. It should also be noted that there are many alternative ways of implementing the methods and apparatuses of the present invention. It is therefore intended that the following appended claims be interpreted as including all such alterations, permutations, and various substitute equivalents as fall within the true spirit and scope of the present invention.

What is claimed is:

1. A spectral reflectometer system for measuring a substrate in a processing chamber, comprising
  a light source;
  at least one optical detector;
  an optical cable, comprising a plurality of optical fibers, wherein the plurality of optical fibers comprises a first plurality of optical fibers, which are transmission optical fibers which extend from the light source to a first portion of a housing supporting the optical cable, and a second plurality of optical fibers, which are reflection optical fibers which extend from the first portion of the housing to the at least one optical detector;
  a second portion of the housing including an optical path for light to traverse through the second portion of the housing; and
  a microlens array in the optical path of the second portion of the housing;
  wherein the housing transmits light from the light source to an illuminated portion of the substrate and collects reflected light from the illuminated portion of the substrate.

2. The spectral reflectometer system, as recited in claim 1, wherein the microlens array decreases spatial distortions including at least one of optical fiber spatial distortion, light source spatial distortion, and collimator spatial distortion.

3. The spectral reflectometer system, as recited in claim 1, wherein the microlens array comprises a plurality of microlens, wherein each microlens of the plurality of microlens has a focal plane, and wherein the illuminated portion of the substrate does not lie on any focal plane of the plurality of microlens so that transmitted light from the light source is blurred on the illuminated portion of the substrate.

4. The spectral reflectometer system, as recited in claim 1, wherein the microlens array is spaced apart from the optical cable.

5. The spectral reflectometer system, as recited in claim 4, wherein the at least one optical detector provides an output as a function of wavelength.

6. The spectral reflectometer system, as recited in claim 5, further comprising a collimator lens in the second optical path, wherein the collimator lens is spaced apart from the microlens array.

7. The spectral reflectometer system, as recited in claim 6, wherein the light source provides a pulsed light.

8. The spectral reflectometer system, as recited in claim 6, wherein the light source provides a continuous wave light.

9. The spectral reflectometer system, as recited in claim 1, wherein at least part of the optical path is substantially perpendicular to the illuminated portion of the substrate, wherein some light reflected from the illuminated portion passes through the microlens array to the optical detector.

10. The spectral reflectometer system, as recited in claim 1, wherein the at least one optical detector provides an output as a function of wavelength.

11. The spectral reflectometer system, as recited in claim 1, wherein the light source is a non-uniform light source.

12. The spectral reflectometer system, as recited in claim 1, wherein the light source is a pulsed Xenon arc lamp.

13. The spectral reflectometer system, as recited in claim 1, further comprising:
   a processing chamber;
   a substrate support for supporting the substrate within the processing chamber;
   a gas source;
   a gas inlet connected between the gas source and the processing chamber;
   a power source;
   at least one electrode adjacent to the processing chamber and electrically connected to the power source; and
   a controller controllably connected to the power source and gas source, and the at least one optical detector, wherein the controller comprises:
      at least one central processing unit; and
      computer readable media, comprising:
         computer readable code for using output from the at least one optical detector to detect an endpoint; and
         computer readable code for changing settings of the power source or gas source when an endpoint is detected.

14. The spectral reflectometer system, as recited in claim 1, further comprising an optical assembly in the optical path.

15. An apparatus for processing a substrate, comprising:
   a processing chamber;
   a substrate support for supporting the substrate within the processing chamber; and
   a spectral reflectometer system, comprising:
      a light source;
      at least one optical detector;
      an optical cable, comprising a plurality of optical fibers, wherein the plurality of optical fibers comprises a first plurality of optical fibers, which are transmission optical fibers which extend from the light source to an optical path, and a second plurality of optical fibers, which are reflection optical fibers which extend from the optical path to the at least one optical detector;
      a microlens array in the optical path, wherein the microlens array comprises a plurality of microlens; and
      an optical assembly supported across the optical path, wherein the optical path is positioned to provide light from the light source to an illuminated portion of the substrate and collect reflected light from the illuminated portion of the substrate, wherein light from the light source and reflected light pass through the microlens array, wherein each microlens of the plurality of microlens has a focal plane, and wherein the illuminated portion of the substrate does not lie on any focal plane of the plurality of microlens.

16. The apparatus, as recited in claim 15, further comprising:
   a gas source;
   a gas inlet connected between the gas source and the processing chamber;
   a power source;
   at least one electrode adjacent to the processing chamber and electrically connected to the power source; and
   a controller controllably connected to the power source and gas source, and the at least one optical detector, wherein the controller comprises:
      at least one central processing unit; and
      computer readable media, comprising:
         computer readable code for using output from the at least one optical detector to detect an endpoint; and
         computer readable code for changing settings of the power source or gas source when an endpoint is detected.

17. The apparatus, as recited in claim 16, wherein the at least one optical detector provides an output as a function of wavelength.

* * * * *